United States Patent
Kerwin

(10) Patent No.: US 10,204,526 B2
(45) Date of Patent: Feb. 12, 2019

(54) ADAPTIVE EXERCISE CIRCUIT TRAINING FOR HEALTH AND FITNESS

(71) Applicant: Patrick Kerwin, Plano, TX (US)

(72) Inventor: Patrick Kerwin, Plano, TX (US)

(73) Assignee: PRIVATE WORKOUT, INC., Plano, TX (US)

(*) Notice: Subject to any disclaimer, the term of this patent is extended or adjusted under 35 U.S.C. 154(b) by 183 days.

(21) Appl. No.: 15/204,794

(22) Filed: Jul. 7, 2016

(65) Prior Publication Data
US 2017/0007885 A1    Jan. 12, 2017

Related U.S. Application Data

(60) Provisional application No. 62/189,472, filed on Jul. 7, 2015.

(51) Int. Cl.
*A63F 9/24* (2006.01)
*G09B 5/02* (2006.01)
(Continued)

(52) U.S. Cl.
CPC ........... *G09B 5/02* (2013.01); *G06F 19/3481* (2013.01); *G09B 5/125* (2013.01);
(Continued)

(58) Field of Classification Search
CPC .......... A63B 2071/065; A63B 21/0628; A63B 24/0075; G09B 5/02
See application file for complete search history.

(56) References Cited

U.S. PATENT DOCUMENTS 5,435,799 A * 7/1995 Lundin ................. A63B 24/00
                                                             482/1
7,846,067 B2   12/2010 Hanoun
(Continued)

FOREIGN PATENT DOCUMENTS

GB    2432795 A    6/2007
WO    8705727       9/1987

OTHER PUBLICATIONS

KINJA Menu / GIZMODO Search "holds-an-internets-worth-of-d-1651327178" "The Best Fitness App" (http://gizmodo.com/5948398/the-best-fitness-apps) (14 pages).

*Primary Examiner* — Steve Rowland
(74) *Attorney, Agent, or Firm* — Shaukat A. Karjeker; David W. Carstens; Carstens & Cahoon, LLP

(57) ABSTRACT

A computer-implemented system for improving a circuit training exercise routine at an exercise facility having at least two pieces of exercise equipment. The system using a smart device, and having steps including: initiating a program on the smart device upon use of a first piece of exercise equipment; displaying exercise instructions to the user on the smart device; initiating a timer on the smart device with a pre-selected amount of time in which the user must complete the exercise instructions on the first piece of equipment; recording if the user is successful in accomplishing the first set of exercise instructions; and prompting the user to move to a second piece of exercise equipment. The steps may also include displaying additional exercise instructions. The system includes monitoring the user's health functions and rewarding the user for successful accomplishment of the first and additional sets of exercise instructions.

14 Claims, 4 Drawing Sheets

(51) Int. Cl.
*G09B 5/12* (2006.01)
*G06F 19/00* (2018.01)
*G09B 19/00* (2006.01)
*G09B 29/00* (2006.01)
*G09B 29/10* (2006.01)
*A63B 71/06* (2006.01)
*A63B 24/00* (2006.01)
*A63B 21/062* (2006.01)

(52) U.S. Cl.
CPC ....... *G09B 19/0038* (2013.01); *G09B 29/007* (2013.01); *G09B 29/10* (2013.01); *A63B 21/0628* (2015.10); *A63B 24/0087* (2013.01); *A63B 71/0622* (2013.01); *A63B 2024/0093* (2013.01); *A63B 2024/0096* (2013.01); *A63B 2071/063* (2013.01); *A63B 2071/065* (2013.01); *A63B 2071/068* (2013.01); *A63B 2071/0625* (2013.01); *A63B 2071/0655* (2013.01); *A63B 2071/0663* (2013.01); *A63B 2071/0691* (2013.01); *A63B 2220/10* (2013.01); *A63B 2220/12* (2013.01); *A63B 2220/14* (2013.01); *A63B 2220/22* (2013.01); *A63B 2220/52* (2013.01); *A63B 2220/62* (2013.01); *A63B 2220/833* (2013.01); *A63B 2220/836* (2013.01); *A63B 2220/89* (2013.01); *A63B 2225/20* (2013.01); *A63B 2225/50* (2013.01)

(56) References Cited

U.S. PATENT DOCUMENTS

| | | |
|---|---|---|
| 7,883,445 B2 | 2/2011 | Olrik et al. |
| 2004/0117214 A1* | 6/2004 | Shea ................ A63B 24/0062 705/2 |
| 2007/0136093 A1 | 6/2007 | Rankin et al. |
| 2007/0219051 A1 | 9/2007 | Hayashino et al. |
| 2007/0219059 A1 | 9/2007 | Schwartz et al. |
| 2011/0201476 A1* | 8/2011 | Solomon ................ G06F 1/1626 482/8 |
| 2011/0281249 A1 | 11/2011 | Gammell et al. |
| 2013/0123068 A1 | 5/2013 | Sultan et al. |
| 2013/0138734 A1 | 5/2013 | Crivello et al. |
| 2014/0067097 A1* | 3/2014 | Harris ................ A63B 71/06 700/91 |
| 2014/0212857 A1 | 7/2014 | Sullivan et al. |
| 2016/0151674 A1* | 6/2016 | Rauhala ................ G09B 5/04 434/247 |

* cited by examiner

ADAPTIVE EXERCISE CIRCUIT TRAINING FOR HEALTH AND FITNESS

CROSS-REFERENCE TO RELATED APPLICATION

This application is a non-provisional application from U.S. Provisional Application 62/189,472 filed Jul. 7, 2015, the disclosure of which is incorporated herein by reference.

BACKGROUND

1. Field of the Invention

The technology presented relates to the field of exercise for purposes of improving health and fitness, and promoting weight loss, if desired. More particularly the technology relates to the use of hand-held and/or wearable electronic devices configured with inter-active applications software to provide an adaptive exercise circuit training routine customized for a particular individual.

2. Description of the Related Art

It is widely known, and of great concern, that the general population is experiencing an increase in rates of obesity, at all age levels. This increase has been linked to an upward trend in certain ailments associated with obesity. Many solutions are being explored, and research is ongoing.

While there are many theories that attempt to address the increasing rates of obesity, many suggest that particular diets or certain "nutritional supplements" may cause an individual to lose weight. With regard to diet, certainly, a high food caloric intake with a relatively lower caloric burn rate will result in weight gain. On the other hand, evidence suggests that even reducing food caloric intake might not lead to weight loss: the human body might respond by going into "starvation mode" to conserve calories and reduce its calorie "burn rate." There are also theories that the nature of the food calories makes a difference. For example, it is now theorized that substitution of a protein calorie rather than a carbohydrate calorie might be beneficial to weight loss. Nutritional supplements have not met FDA guidelines to be able to make a credible claim that any of them promote safe weight loss.

It is theorized that the human body was adapted over past centuries to daily hard work, walking (or running) and to having a relatively meager food caloric intake. In other words, regular daily exercise and a restricted calorie diet. Of course, all of this might also not be recommended for optimum human growth, health and strength. More affluent times have brought about an improvement in nutrition, and in the variety of available nutritious foods, and better medical care. Humans have grown taller as result, and their longevity has increased. However, affluent times have also, especially in recent years, coincided with the so-called "obesity epidemic."

Regardless of the theories advanced as causes for (un-wanted) weight gain, and whether that weight gain relates directly to a variety of ailments, many believe that they can improve their health and fitness through regular exercise. Medical professionals routinely advise patients to exercise regularly, as a way to achieve (or maintain) good health. However, compliance with the medically-supported suggestion is low. Exercise is perceived by many as "no fun," and is often, at least initially, associated with pain, which is associated with exercise of muscles that are unaccustomed to being taxed by exercise. The initial pain discourages ongoing perseverance and compliance. Furthermore, even the use of a personal trainer, which is intended to provide a "personal motivational coach" and an incentive to exercise at regularly scheduled sessions, might not be sufficient motivation. In addition, in the fast-paced, hectic business world, there is the time factor: there are only so many waking hours in the day, and one has to prioritize business needs, family needs, social needs, and exercise needs. Thus, the "lack of time" factor is often the reason for the non-compliance, or failure, of the most well-intentioned person to exercise regularly, and his/her subsequent decline into weight gain and/or declining health.

SUMMARY

An exemplary embodiment of the adaptive exercise circuit training routine customized for a particular individual ("trainee") includes a hand-held device or a wearable device, such as a smartwatch having a graphic user interface ("GUI"), that is preferably touch or voice activated. The device is configured with an applications software-based inter-active program that from which the trainee can select via the GUI a circuit-training program customized for the particular trainee. In one aspect, the trainee performs a single exercise for a pre-set amount of time (e.g., two minutes) based on applications software instruction, viewable in the GUI, before progressing to the next station. Optionally, instead of using a circuit-training program customized for the particular trainee, the trainee may select between different "challenge levels" (e.g., beginner, intermediate, advanced, or expert) before beginning the exercise routine. The application will then compile an appropriate set of exercises based on the challenge level selected.

In an exemplary embodiment, the circuit training program may commence by instructing the trainee to perform a routine of a series of exercises that each includes a pre-set numbers of repetitions of a particular exercise, but under different loads. Prior to the trainee commencing the series of exercises, the trainee may view a video tutorial of the exercise provided by the circuit training program, visible to the trainee on the GUI, during the training session. These video tutorials may include, for example, exercises to be performed and images of a model trainer demonstrating the proper form of the exercise at different phases. If the trainee has already seen the tutorial, the trainee will be prompted to access the first of the series of pre-set numbers of repetitions of a particular exercise, under different loads. This series of exercises may, for example commence with a first set of eighteen repetitions of the exercise ("reps") using a lighter amount of weight. Thereafter, for example, the circuit training program may instruct the trainee via the GUI to perform a second series that includes a set of six reps using a heavy amount of weight. Finally, the circuit training program may instruct the trainee to perform a third series that includes a set of twelve reps using a moderate amount of weight. For each set of reps, the trainee updates his/her data by inputting via the GUI of the device how many reps he/she was actually able to successfully accomplish. Input data may be stored on the device, and/or may be transmitted to a database, which may be at a remote facility. The stored data is accessible by the trainee for review, and the data may be correlated by the trainee with past performance, using the circuit training software program, to provide information regarding changes in performance relative to prior sessions. The data may optionally be displayed graphically, to more clearly visually display performance trends over time. Further, optionally, when pre-specified program goals are met, the trainee may be rewarded appropriately by a message, a gift, or another form of motivational encouragement.

In an exemplary embodiment, a device equipped with interactive software-enabled adaptive exercise circuit training routines may use a slider bar (or similar graphical interface) to easily allow the trainee to indicate the number of reps performed. Or, it may allow voice commands to input such information. The application may also use a timer to track the elapsed time during which the trainee was able to perform the particular set at the given weight. This is readily input either manually, or by voice command, such as "start timing" and "end timing" to determine elapsed time. Optionally, the device may keep track of the total time spent on the circuit training program exercise routine and provide visual, auditory, or tactile feedback (vibration of smartphone or watch, for example) to the trainee to indicate that the time limit for the particular exercise is approaching, or has been exceeded.

In a further exemplary embodiment, a device equipped with an adaptive exercise circuit training routine may also be equipped with hardware to monitor body statistics, such as heart rate, blood pressure, and blood glucose level. The trainee may also input his/her weight to the device via the GUI to facilitate review of performance, and to track weight, as well as measuring body mass index ("BMI"). Further, optionally, the trainee may input, or the device may be able to monitor and track, the trainee's percentage body fat.

In an exemplary embodiment, a device equipped with an adaptive exercise circuit training routine tracks the trainee's progress and uses the trainee's relative success at a particular exercise set to automatically adjust the reps, weight/load, and/or type of exercise in the future. In other words, the application adapts future routines for a trainee based on the current and past performance of that trainee.

BRIEF DESCRIPTION OF THE DRAWINGS

Aspects of the novel and inventive technology and many of the attendant advantages, of the present technology will become more readily appreciated by reference to the following Detailed Description, when taken in conjunction with the accompanying simplified drawings of illustrative and exemplary embodiments. The drawings briefly described here below are not to scale, are presented for ease of explanation and do not limit the scope of the inventions recited in the accompanying patent claims.

DETAILED DESCRIPTION

The following non-limiting detailed descriptions of examples of embodiments of the invention may refer to appended Drawings and are not limited to the drawings, which are merely presented for enhancing explanations of features of the technology. In addition, the detailed descriptions may refer to particular terms of art, which are defined herein, as appropriate and necessary for clarity.

The term "circuit training exercise program" as used in the description and patent claims refers to a particular kind of exercise training which includes a series of sets of repetitions of a particular exercise (or exercises) performed by the trainee in a specified order, and at a specified tempo and/or within a specified time period. There is a specified recovery time, before the next series of sets of exercises commences. For example, and only for non-limiting illustrative purposes, a series of exercises may be arm curls with weights. There may be three sets to the series. The first set may be twelve arm curl repetitions ("reps") with a light weight load, carried out in 40 seconds. There may be a recovery time break of 30 seconds, then a second set may commence that may include, for example, eight arm curl reps with a heavier weight performed within 30 seconds. This may be followed by a recovery time break of 30 seconds. Then a third set of ten arm curl reps at an intermediate weight, to be performed in 45 seconds.

Figure 1:
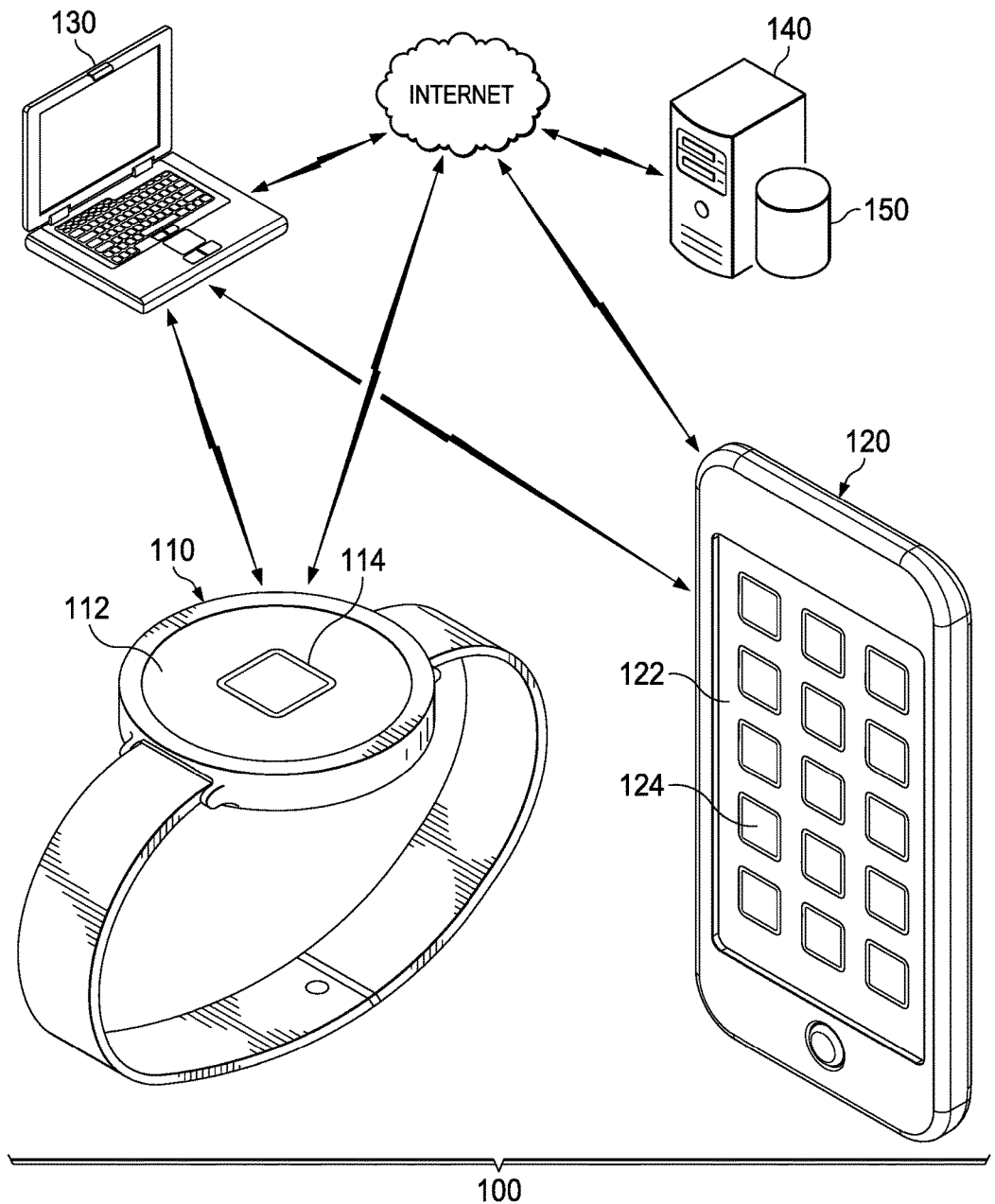
FIG. 1 is a schematic representation of exemplary devices that may be used in connection with the inventive technology.

Referring to FIG. 1, devices 100, exemplified by a smart watch 110 and a smartphone 120, are useful in the present technology. Preferably, for ease of use, the devices 100 are each equipped with a touchscreen graphic user interface 112, 122 that displays interactive applications software ("apps") icons 114, 124 on the device 100. The trainee uses the appropriate icon to access the interactive applications software that will provide the guide, prompts and tutorials to take him/her through the circuit training program. The interactive applications software will also allow user input, and storage of input data. As explained here below, it has many additional features.

The devices 100 may download data from a completed circuit training exercise program to a computer, such as the illustrated laptop 130, via Bluetooth® or another wireless protocol, or through a wired connection. Data downloaded to a computer 130 may then be communicated via the Internet, for example, to a server 140 having a database 150 that accumulates data for each authorized user/trainee. Alternatively, or in addition, the devices 100 may have the capability to communicate data to and from a remote server 140 having a database 150, via the Internet.

Figure 2:
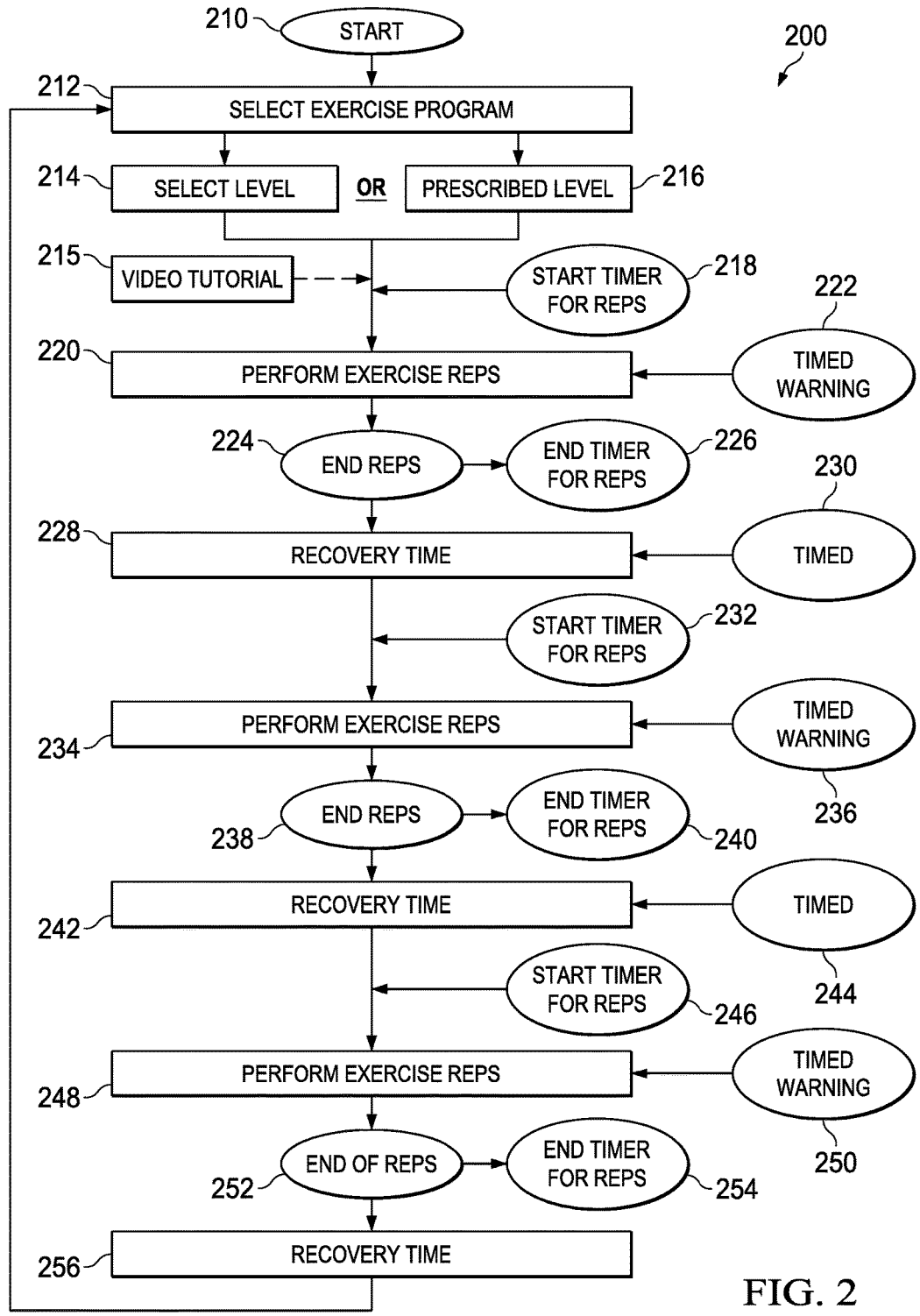
FIG. 2 is a flow chart depicting an exemplary embodiment of at least some of the features and steps that a hand-held device or a wearable device configured with exemplary applications software performs in guiding a trainee through an exemplary adaptive circuit training program.

FIG. 2 illustrates some aspects of an exemplary embodiment of the applications software 200 that is loaded onto the devices 100, and interactively accessed through the GUI 112, 122 via the appropriate icon 114, 124, respectively. To commence a circuit training exercise program session, the trainee will open the applications software 200, at block 210. Then, the trainee selects a particular series of circuit training exercises, at block 212, from several choices presented. After this selection, the trainee can either select a level of the circuit training exercise program selected, such as "beginner," "advanced," or "expert", in block 214, or the adaptive software application will use past data for this trainee to present a prescribed level of exercise, in block 216.

Before commencing exercises, the trainee may view a video tutorial with a demonstration of how to appropriately perform the selected exercises in proper form, as shown by a model coach, in block 215. If the trainee feels comfortable doing so, he/she can skip the tutorial step 215 and advance once a level of the circuit training exercise program has been selected, or the prescribed level has been accepted. A timer 218 may start in order to record the time taken for the exercise reps, for example arm curls, and to compare against a prescribed time limit for the number of exercise reps. The trainee is prompted to commence the first timed set of reps of the circuit training exercise program routine, in block 220. If the trainee fails to complete the number of reps in the allotted time, he/she receives an audible or tactile warning signal, block 222. Once the reps are completed in 224, or when a time-over signal is received from block 222, the trainee has a recovery period break (block 228) of a predetermined period of time, as set in block 230, by the circuit training exercise program. The trainee can use this recovery time to input his/her number of completed reps, if the target number of reps set by the selected or prescribed level is not met.

After the recovery time, the device 100 provides a timed warning 232 and starts the timer for the second set of timed reps, in block 234. These reps are timed in timer block 236. As before, the reps are timed, and a time-elapsed warning signal from block 236 may issue, if the trainee fails to complete the set number of reps in the allotted time. When the end timer 240 indicates time has elapsed, the trainee ends reps 238, and has a recovery time break 242 that is timed 244. During the recovery time break, the trainee can input data to the interactive applications software, such as for example the number of reps completed, if all reps for the set could not be completed in the allotted time. After a timed (block 244) recovery period, a start timer 246 commences the time for the next (and in this example) last set of reps. Of course, any number of sets may be set as needed, for any circuit training exercise program, tailored for the trainee. The trainee then performs the timed set of reps, block 248, and the timer issues a warning signal (block 250) when the pre-set time for the set of reps has elapsed. At the end of the pre-set time period for the reps, block 252, the time taken for the reps is recorded (block 254) by user input via the GUI. A final recovery time 256 commences. After this recovery time, a next series of the circuit training exercise program can be initiated by going to the start, block 212, and performing a different exercise.

Figure 3:
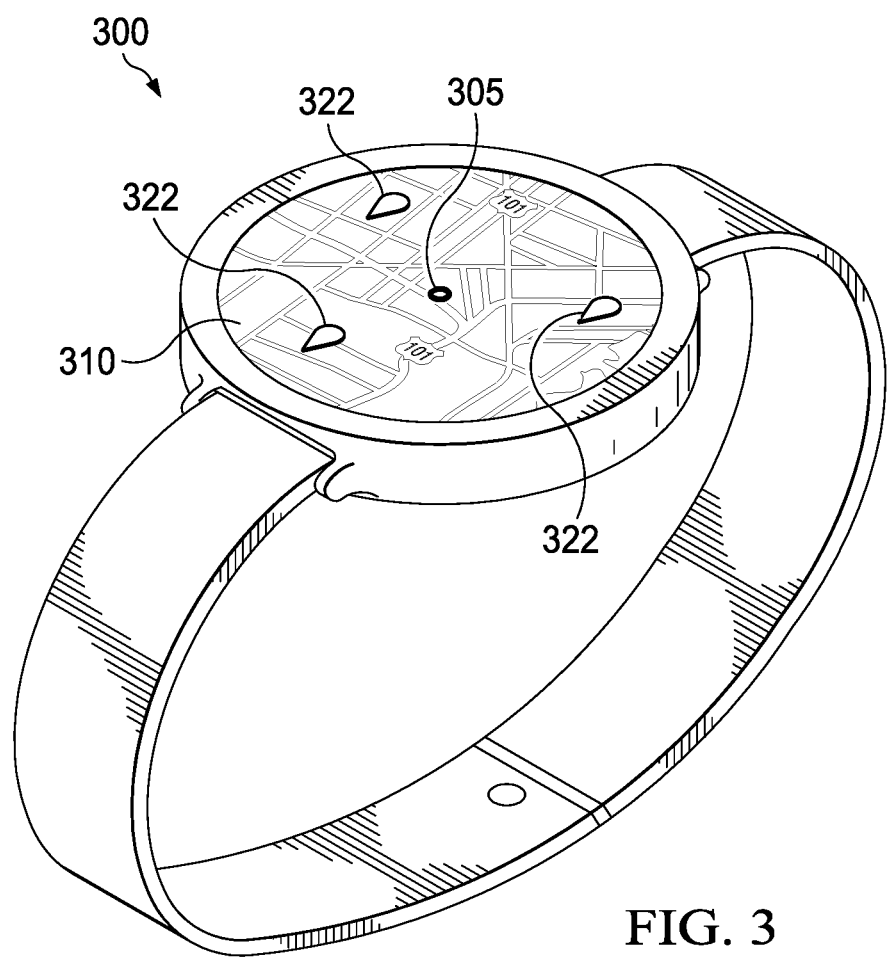
FIG. 3 is a schematic depiction of an exemplary embodiment of wearable technology including an app displaying data, the data including nearby exercise locations and equipment in the locations, thereby permitting user selection of an exercise facility for the user's circuit training exercise program.

In a further exemplary embodiment, illustrated in FIG. 3, that is especially useful for a user that has a customized circuit training exercise program and who is away from his usual location (travelling, for example), there is provided an app on a mobile communications device equipped with GPS. The device 300 may be a wearable device, such as a smart watch 300, or a cell phone or a mobile tablet. Using GPS and the location of the user, the device is configured to display the location of the user 305 on a map graphic 320 on a graphic user interface 310 of the device and also to display on the map the locations 322 of any nearby gyms. The user may then select a nearby gym, and the app is configured to then display the equipment available at the gym that the user's customized circuit training exercise program workout program requires. Any exercises that are part of the user's circuit training exercise program that cannot be catered for by the particular gym's equipment are highlighted. Alternative equipment that may also meet the user's customized circuit training exercise program are suggested. Based on this information, the user can select a gym foe exercising.

Figure 4:
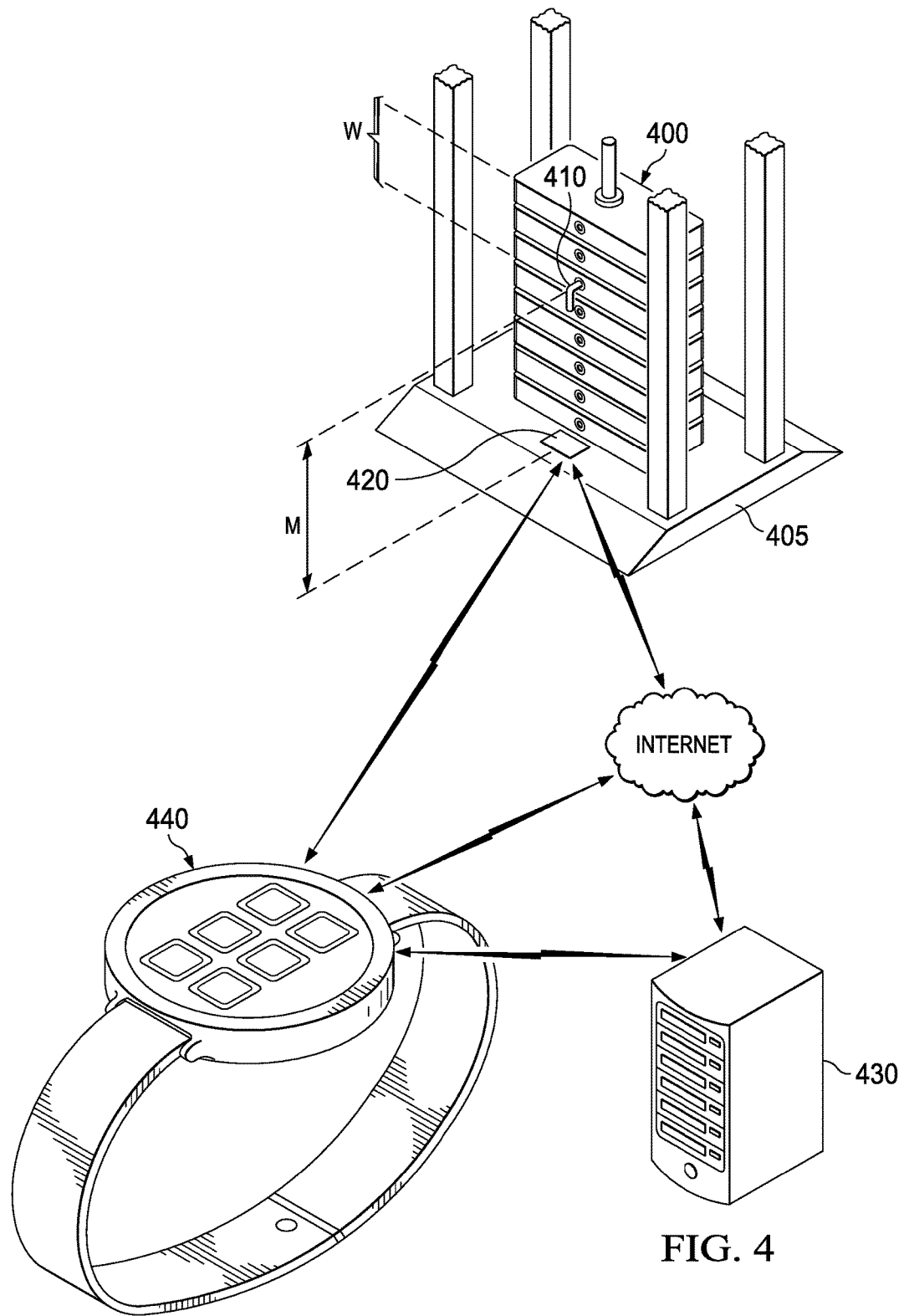
FIG. 4 is a schematic depiction of an exemplary embodiment including interaction between an app on a user's wearable device and exercise equipment capable of sensing and transmitting data.

In a further exemplary embodiment, illustrated in FIG. 4, the exercise equipment is retrofitted or modified to include a capability to measure the amount of weight (mass) that a user lifts, the number of repetitions, and the time interval between repetitions. This information is captured, stored and transmitted. Using this automated system, the user is freed from the task of inputting the number of reps completed on a particular machine. Instead, an app on a mobile communications device of the user detects and records the machine used, the exercise performed on the machine, the number of reps completed, and the interval between a series of reps. The example illustrated depicts schematically a stack of weights 400 where each weight (in this example) is of approximately equal thickness and equal weight. Thus, when a weight locator pin 410 is inserted into a weight, at a height M from the base 405 of the stack, the distance M is sensed by sensor 420. Based on the sensed height M and the thickness of the weights, the number of weights W that the user will lift, and the total mass can be readily calculated. Thus, when the user approaches the machine, a mobile communications device of the user configured with an app, illustrated as a smart watch 440, the sensor 420 of the machine transmits, via near field communications technology, for example, the identity of the machine to the smart watch app. The sensor 420 in turn identifies the user by communications with identifying data on the app on the user's smart watch 440. The app on the watch is configured with the user's customized circuit training exercise program, and using this information and the identity of the machine, the app displays for the user the weight he/she should select (W) to exercise on the machine, the number of reps, the rest interval (recovery time break) between reps, and the number of sets of reps to complete. As the user begins to exercise, the weight W moves upward away from the sensor 420. The distance and speed of the movement of weight stack W between locator pin 410 and sensor 420 is measured and recorded for each rep, as well as the length of time interval pauses between each time the weight is moved. In addition, the number of completed reps is sensed and these are also recorded. Locator pin 410 is equipped with an accelerometer and a transmitter to enable this data gathering and communication. Thus, the sensed data may be transmitted from sensor 420 to the smart watch 440 equipped with the app, and thence to a local server 430, and via the internet (I) to a cloud-based (or other) database where the data may be analyzed and reviewed by a trainer for user performance and user progress. Other data handling, storage and data analysis schemes may also be used. Significantly, however, the automated system relieves the user from the task of data input, and it permits the automated recording of the performance of the user in his/her customized circuit training exercise program.

While examples of embodiments of the technology have been presented and described in text and some examples also by way of illustration, it will be appreciated that various changes and modifications may be made in the described technology without departing from the scope of the inventions, which will be set forth in, and only limited by, the scope of patent claims to be appended, as properly interpreted and construed.

The invention claimed is:

1. A computer-implemented system for improving circuit training exercise routine at a facility having at least two pieces of exercise equipment, each of which have at least two weight settings, said system using a using a smart watch, said system allowing a user as an exerciser to:
   initiate a program on the smart watch upon use of a first piece of exercise equipment;
whereupon the system carries out steps comprising:
   displaying a first set of exercise instructions to the user on the smart watch;
   initiating a timer on the smart watch with a pre-selected amount of time in which the user must complete the exercise instructions on the first piece of equipment;
   detecting and recording if the user is successful in accomplishing the first set of exercise instructions;

prompting the user to move to a second piece of exercise equipment;
displaying a second set of exercise instructions to the user on the smart watch;
initiating a timer on the smart watch with a pre-selected amount of time in which the user must complete the exercise instructions on the second piece of equipment;
detecting and recording if the user is successful in accomplishing the second set of exercise instructions;
monitoring the user's health functions; and
rewarding the user for successful accomplishment of the first and second set of exercise instructions.

2. A computer-implemented system for improving a circuit training exercise routine at a facility having at least two pieces of exercise equipment, each of which have at least two weight settings, said system using a using a smart watch, said system allowing a user to:
initiate a program on the smart watch upon use of a first piece of exercise equipment;
whereupon the system carries out steps comprising:
displaying a first set of exercise instructions to the user on the smart watch;
initiating a timer on the smart watch with a pre-selected amount of time in which the user must complete the exercise instructions on the first piece of equipment;
detecting and recording if the user is successful in accomplishing the first set of exercise instructions; and
prompting the user to move to a second piece of exercise equipment.

3. The system of claim 2, further comprising the steps of:
displaying a second set of exercise instructions to the user on the smart watch;
initiating a timer on the smart watch with a pre-selected amount of time in which the user must complete the exercise instructions on the second piece of equipment;
detecting and recording if the user is successful in accomplishing the second set of exercise instructions.

4. The system of claim 2, further comprising: monitoring the user's health functions; and
rewarding the user for successful accomplishment of the first and second set of exercise instructions.

5. The system of claim 2, further comprising a step of allowing an exerciser to view a video tutorial about an exercise before the exerciser commences the exercise.

6. The system of claim 2, wherein the system includes a step of allowing a user to select between "beginner," "advanced," and "expert" levels of exercise an exerciser using the smart watch.

7. The system of claim 2, wherein past performance data of an exerciser is used to present a prescribed level of exercise.

8. The system of claim 2, wherein an audible warning is sounded when a user fails to complete a set of exercises within the pre-selected time.

9. The system of claim 3, wherein a timed recovery time is allotted between the first set of exercises and the second set of exercises.

10. A computer-implemented system for improving a circuit training exercise routine at a facility having at least two pieces of exercise equipment, each of which have at least two weight settings, said system using a using a smart watch, said system allowing a user as an exerciser to:
initiate a program on the smart watch upon use of a first piece of exercise equipment;
whereupon the system carries out steps comprising:
allowing the user to optionally view an instructional video tutorial about a first set of exercises;
displaying a first set of exercise instructions to the user on the smart watch;
initiating a timer on the smart watch with a pre-selected amount of time in which the user must complete the exercise instructions on the first piece of equipment;
detecting and recording if the user is successful in accomplishing the first set of exercise instructions;
prompting the user to move to a second piece of exercise equipment;
allowing the user to optionally view an instructional video tutorial about a second set of exercises;
displaying a second set of exercise instructions to the user on the smart watch;
initiating a timer on the smart watch with a pre-selected amount of time in which the user must complete the exercise instructions on the second piece of equipment;
detecting and recording if the user is successful in accomplishing the second set of exercise instructions;
monitoring the user's health functions;
rewarding the user for successful accomplishment of the first and second set of exercise instructions; and
using data about past performance of the user to set an exercise level for a next session of exercise for the user.

11. The system of claim 10, wherein the exercise level is selected from: "beginner," "advanced," and "expert" levels of exercise.

12. The system of claim 10, wherein the user is allowed to select from: "beginner," "advanced," and "expert" levels of exercise.

13. The system of claim 1, wherein a user is allowed to input data to the system.

14. The system of claim 10, wherein a user is allowed to input data to the system.

* * * * *